United States Patent [19]

Rojey et al.

[11] Patent Number: 4,775,395
[45] Date of Patent: Oct. 4, 1988

[54] INTEGRATED PROCESS FOR THE TREATMENT OF A METHANE-CONTAINING WET GAS IN ORDER TO REMOVE WATER THEREFROM

[75] Inventors: Alexandre Rojey, Garches; Joseph Larue, Chambourcy, both of France

[73] Assignee: Institut Francais du Petrole, Rueil-Malmaison, France

[21] Appl. No.: 109,005

[22] Filed: Oct. 16, 1987

[30] Foreign Application Priority Data

Oct. 16, 1986 [FR] France .................................. 86 14504

[51] Int. Cl.$^4$ ........................................... B01D 53/14
[52] U.S. Cl. ........................................... 55/27; 55/30; 55/31; 55/32; 55/48; 55/50; 55/51; 55/89; 55/93
[58] Field of Search ................... 55/27, 29, 30, 31, 32, 55/48, 50, 51, 88, 89, 93

[56] References Cited

U.S. PATENT DOCUMENTS

| | | | |
|---|---|---|---|
| 2,318,752 | 5/1943 | Carney | 55/88 |
| 3,214,890 | 11/1965 | Sterrett | 55/88 X |
| 3,664,091 | 5/1972 | Hegwer | 55/29 |
| 3,886,757 | 6/1975 | McClintock et al. | 55/31 X |
| 4,057,403 | 11/1977 | Valdes | 55/31 |
| 4,529,413 | 7/1985 | Ferguson | 55/32 |
| 4,606,741 | 8/1986 | Moreau et al. | 55/73 X |

*Primary Examiner*—Kathleen J. Prunner
*Attorney, Agent, or Firm*—Millen & White

[57] ABSTRACT

A gas containing methane and water is treated in order to remove water therefrom. The process comprises a step of contacting the gas with a liquid phase formed of water and solvent, whereby water free of solvent can be removed, and a subsequent step of cooling the resultant gas. The process is applicable to natural gas and to refinery gas.

17 Claims, 3 Drawing Sheets

INTEGRATED PROCESS FOR THE TREATMENT OF A METHANE-CONTAINING WET GAS IN ORDER TO REMOVE WATER THEREFROM

BACKGROUND OF THE INVENTION

The treatment of a gas, either natural gas or refinery gas, generally comprises a dehydration step employed to avoid problems of hydrate formation and of corrosion during transportation. The treatment may also comprise a step of separating higher hydrocarbons, for example C2 to C5 (LPG) hydrocarbons by cooling so as to adjust the dew point of hydrocarbons in order to avoid condensation during transportation, or to recover a LPG fraction easier to upgrade than the treated gas. It is also necessary to adjust the content of acid gases, particularly of $H_2S$ and $CO_2$.

The steps of treatment are generally independent. According to the known techniques:

The dehydration may be performed by washing with a solvent which is mostly a glycol such as diethyleneglycol (DEG). This solvent must be regenerated by distillation.

The LPG separation is performed by cooling at a temperature which must be the lower as the desired LPD recovery rate is higher.

The deacidification is performed by washing with a physical solvent (for example polyethylene glycol dimethylether=PEGDME or propylene carbonate) or a chemical solvent (amine). This solvent must be regenerated by distillation. According to French patent application No. 2,550,956, the purification of natural gas may be performed by washing the gas with liquid methanol. Methanol absorbs the impurites and must then necessarily be regenerated by distillation. According to the published United States patent application Ser. No. B 421,383, a wet gas is washed with methanol to remove therefrom at least a part of its water. A water-methanol phase is recovered which must be regenerated by distillation. The regeneration of the solvent may be performed for example by the method disclosed in European patent application No. 0,053,424.

SUMMARY OF THE INVENTION

It has been discovered that the dehydration, alone or associated with an LPG separation and/or a deacidification, may be performed in a single operation of treatment, with a substantial saving in investment as well as in bulk and equipment weight, which is particularly advantageous for such activities as natural gas offshore production.

It has also been discovered that these treatment operations may be performed with a proportion of solvent which is much lower than the usual solvent proportion in solvent washing operations.

It has also been discovered that the solvent used may be regenerated without recourse to a distillation step, this resulting in many advantages: savings in investment as well as in bulk and weight of the equipment, reduction in power consumption, and the possibility of avoiding heating by combustion, which is highly advantageous in the activity of natural gas offshore production.

BRIEF DESCRIPTION OF THE DRAWINGS

The invention will now be described more in detail, by way of illustrative and non-limiting example, with reference to FIGS. 1 to 5 of the accompanying drawings wherein.

Figure 1:
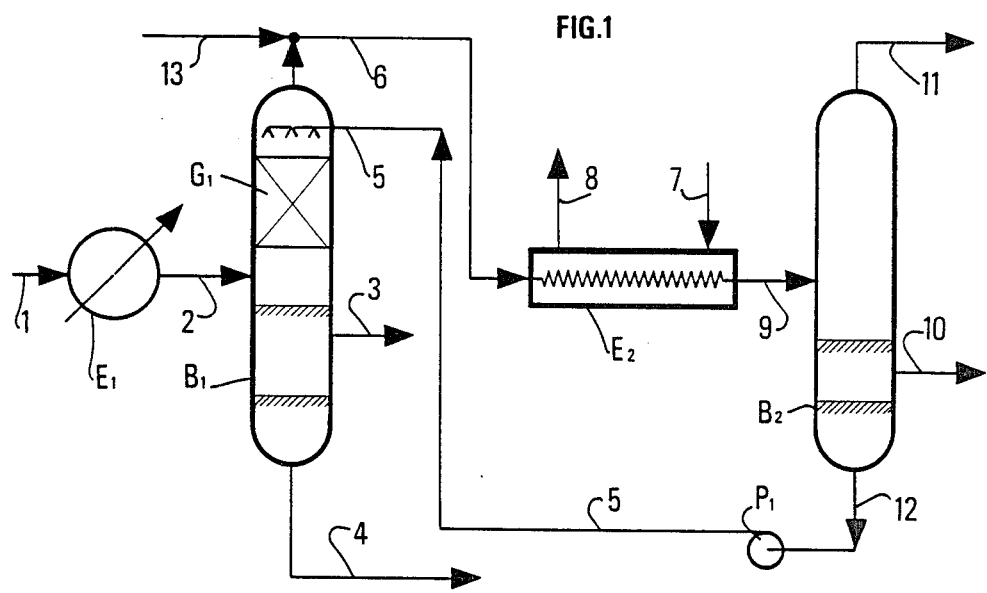
FIG. 1 is a flowsheet illustrating an embodiment of the invention adapted, for example, to the treatment of a natural gas containing associated higher hydrocarbons.

The principle of the process according to the invention is illustrated by the flowsheet of FIG. 1 applied for example to the treatment of natural gas containing associated higher hydrocarbons.

The gas to be treated is supplied through line 1. It is cooled by the available coolant, for example water or air, in exchanger E1, wherefrom it is discharged through line 2. This first cooling step provides for the separation of a liquid gasoline fraction formed by hydrocarbons condensable at the temperature and pressure conditions prevailing at the output of exchanger E1, said fraction being discharged through line 3, and an aqueous fraction which settles in the contact column B1 bottom and is discharged through line 4. The remaining gas is saturated with water.

This first cooling step is not always compulsory, particularly when the gas to be treated is already available at relatively low temperature.

The gas is then contacted with a liquid phase formed of water-containing solvent originating from the separation column B2 and conveyed through line 5 to a contact zone G1 formed, for example, of packing. The gas discharged from the contact zone contains steam and solvent, mostly in amounts close to saturation. The contact between the gas and the liquid phase in the contact zone G1 is preferably performed countercurrently.

The operations performed in the contact zone G1 and in the column B1 are not necessarily performed as a whole in a single enclosure. In particular, the liquid phases recovered at the output of exchanger E1 may be separated in a different enclosure. On the other hand various geometries favoring the decantation of the liquid phases, for example by increasing the residence time, may be used for the column B1.

It has been discovered that the stripped solvent in the gas phase at the output of contact zone G1 may suffice to avoid hydrate formation problems associated with the cooling step destined to separate the LPG fraction.

It has also been discovered that said cooling step also provides for the dehydration of the treated gas, provided that the formation of hydrates be avoided by the specified means.

The gas flowing out from contact zone G1, saturated with water and solvent, is discharged through line 6.

It is then cooled in exchanger E2 with a coolant supplied through line 7 and discharged through line 8.

It flows out from exchanger E2 through line 9. The cooling performed in exchanger E2 results in the condensation of a LPG fraction which is discharged through line 10. It also provides for the condensation of the major part of water and solvent contained in the gas supplied to exchanger E2 through line 6. Thus a liquid phase is obtained which is formed of a mixture of water and solvent immiscible with the LPG liquid phase and which is discharged from column B2 through line 12 and recycled through pump P1 and line 5 to contact zone G1.

In contact zone G1, the recycled liquid phase fed through line 5 and formed of a solvent-water mixture, is contacted with the gas supplied through line 2, which is saturated with water and contains no solvent. The solvent of the recycled liquid phase is at least in major part vaporized and stripped by the gas phase whereas water of the recycled liquid phase, which cannot be stripped by the gas already saturated with water, is recovered at the bottom of column B1, at least in major part freed of solvent. The solvent concentration of water discharged through line 4 is generally lower than 10%, preferably lower than 5%, for example from 0.01 to 5%. The water-solvent separation is thus achieved by contact with the gas to be treated without requiring a regeneration of said solvent by distillation.

According to the process of the invention, the solvent is subjected to a cycle: it is successively vaporized by the treated gas in the contact zone G1, condensed together with water during the cooling phase in exchanger E2 to form a liquid phase separate from the gas phase and from the hydrocarbon liquid phase in column B2, and recycled to the contact column through pump P1 and line 5. Although the solvent is thus recycled in the process, an additional solvent amount may be supplied through line 13 to compensate for the losses resulting from solvent traces stripped in lines 4, 10 and 11. The additional amount supplied through line 13 depends on the operating conditions of the process: it is generally lower than 20% and preferably lower than 5% of the solvent amount contained in the recycled solution flowing through line 5. The solvent solution recycled through line 5 is formed by a major part of the water and solvent present in the gas at the output of the contact column in line 6, which is condensed by cooling in exchanger E2. Consequently, the water and solvent amounts contained in the recycled solution flowing through line 5 are substantially the same as those contained in the gas as vapor at the output of the contact column.

The solvent amount contained in the recycled liquid phase flowing through line 5 corresponds to the concentration with respect to water required to inhibit the formation of hydrates and/or ice in the treated gas during the cooling stage in exchanger E2. This concentration must be the higher as the temperature of column B2 is lower. It is preferably from 10 to 90% by weight. It may be estimated by different methods known in the art, for example by the Hammerschmidt formula currently used in the domain of natural gas. The solvent amount contained in said recycled liquid phase is hence in relation with the water amount contained as steam in the gas to be treated feeding the contact column and is substantially of the same magnitude. Hence, the process according to the invention does not involve a gas washing by a solvent phase having for an object to absorb the water contained in the gas, which implies the use of solvent amounts much higher than, and currently equal to 10-100 times, the water amount contained in the gas. In the process according to the invention, the recycled solvent amount is such that the gas to be treated flowing out from contact column B1 through line 6 contains, as vapor, the major part (currently more than 90%) of the recycled solvent and the major part (currently more than 50%) of its water content at the input of contact zone G1.

Finally, the process according to the invention comprises the following steps of:

(a) Contacting the gas to be treated, preferably countercurrently, with a recycled liquid phase containing both water and a solvent, the contact conditions being selected so as to vaporize and transfer at least 90% of said solvent into said gas, discharging the aqueous liquid phase resulting from said contact, which contains less than 10% of the recycled solvent amount, and recovering said gas containing as vapor at least 90% of said solvent contacted with the gas, said solvent being a non hydrocarbon compound other than water, miscible with water. Preferably said contact is characterized in that the water and solvent amounts contained in said recycled liquid phase are substantially the same as those contained in said gas recovered after contact.

(b) Cooling the gas from step (a) so as to produce the condensation of a liquid fraction essentially formed of solvent and water.

(c) Separating the gas from said liquid fraction and recycling and liquid fraction containing both solvent and water to step (a).

Preferably, a solvent make-up is added to compensate for the losses. Advantageously, this solvent make-up is introduced in the gas originating from step (a) before proceeding to step (b).

The proportion of vaporized solvent during the contact operation of step (a) may be adjusted by controlling the temperature, the pressure and the relative proportions of gas and recycled liquid phase.

When the gas further contains at least one hydrocarbon other than methane, condensable in the conditions of step (b), thus forming a hydrocarbon liquid fraction separate from said fraction essentially formed of solvent and water, said hydrocarbon liquid fraction is separated and discharged from the process.

EXAMPLES

The following examples are given to illustrate the invention and must not be considered as limiting the scope thereof.

The principle of the process according to the invention is illustrated by example 1.

EXAMPLE 1

This example is conducted in accordance with the flowsheet of FIG. 1. The gas to be treated, which is an associated gas from an oil well, is fed through line 1, at a temperature of 60° C., a pressure of 4 MPa, at a rate of 56,100 kg/h. It is saturated with water. It is cooled by heat exchange with water to a temperature of 20° C. in heat exchanger E1 wherefrom it flows out through line 2. This cooling produces the condensation of 2,000 kg/h of liquid gasoline and of 207.9 kg/h of liquid water. The mixture of uncondensed gas with both liquid phases is supplied to column B1: two liquid phases are separated in the bottom of column B1; the gasoline phase is discharged through line 3. The remaining gas, saturated with water (28.5 kg/h), is countercurrently contacted at 20° C. in a packing G1 with a liquid phase formed of methanol-water mixture originating from column B2 and supplied through line 5. The aqueous phase settles in the bottom of column B1 and is discharged through line 4 at a rate of 237 kg/h, corresponding to 236.3 kg/h of water and 0.7 kg/h of methanol. It is formed in major part (207.9 kg/h) of condensed water supplied with the gas through line 2 and in part (29.1 kg/h) of water originating from the packing zone G1 of gas-liquid contact (containing said 0.7 kg/h of methanol). The water-methanol mixture flows through line 5 at a rate of 88.2 kg/h. It contains 28% by weight of water and 72% by weight of methanol. The gas (53,951.2 kg/h, dischraged from column B1 through line 6, is saturated with water (24.8 kg/h) and with methanol (62.8 kg/h, i.e 98.9% of the methanol charge). It is cooled to a temperature of $-40°$ C. in heat exchanger E2 by means of an external coolant fed through line 7 and discharged through line 8. This cooling produces a condensation of liquid hydrocarbon (natural gas liquid) and of the major part of water and methanol.

The purified gas and the two liquid fractions are separated in column B2. The water-methanol fraction flows out from column B2 through line 12 and is recycled, through pump P1 and line 5, to column B1. The liquid hydrocarbon fraction is discharged through line 10 at a rate of 15,600 kg/h.

A solvent make-up destined to compensate the losses and to maintain stable operating conditions is performed through line 13. As shown in said example, the process may operate with a reduced solvent circulation since the molar ratio of the solvent flow rate conveyed through pump P1 to the gas flow rate is about 1/780.

Generally this ratio remains lower than 1/10 and even may be lower than 1/100, as shown in the preceding example. It is usually from 1/5,000 to 1/10, for example from 1/1,000 to 1/10.

Another essential advantage of the process, as apparent from said example, is that the solvent phase is regenerated without requiring any distillation.

Figure 4:
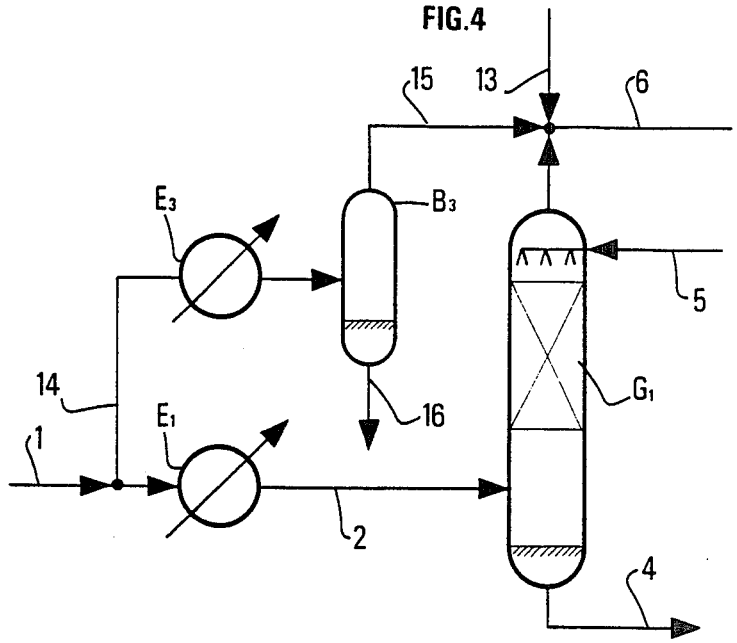
FIG. 4 illustrates an embodiment where only a fraction of the feed gas is contacted with the recycle solution.

The amount of recycled solvent solution flowing through line 5 being low as compared to the gas amount, it is unnecessary to contact the totality of the gas to be treated with the recycled solution in contact zone G1, and a portion of said gas may be by-passed. The principle of said configuration is illustrated in FIG. 4. The gas to be treated, supplied through line 1, is divided into two parts: one part is supplied to exchanger E1, then to the contact column through line 2 and is contacted with the recycled solution conveyed though line 5, exactly as in the embodiment of FIG. 1. The other part of the gas to be treated passes through line 14 and is cooled in exchanger E3, thereby condensing a water fraction which is separated in column B3 and discharged through line 16. The gas flowing out through line 15, saturated with water, is admixed with the gas originating from contact zone G1 which contains the solvent in gas phase. The whole gas flow is conveyed through line 6, to exchanger E2 for being cooled, as in the embodiment of FIG. 1. The fraction of treated gas contacted with the recycled liquid solution may here correspond to the minor fraction of the gas to be treated and ranges for example from 10 to 50% thereof.

This configuration offers many advantages: it makes possible to regenerate the solvent with the strictly necessary gas amount. Moreover it leads to a liquid/gas ratio closer to that used with conventional contact means such as those of the packing type, for example. Moreover, the temperature conditions of the contact means may be adjusted to a value different from that of column B3 in order to optimize the whole flow-sheet.

Depending on the composition of the treated gas, the LPG amount condensed in column B2 may be much higher than the also condensed solvent-and-water solution amount, currently 10 to 100 times the latter. Although the solvent is not much soluble in the LPD liquid phase, the solvent amount dissolved therein may currently amount to 1/50-½ of the total solvent amount condensed in column B2. The solvent contained in the LPG liquid phase flowing through line 10 may be recovered by washing of the LPG liquid phase by means of water, thus producing a LPG liquid phase free of solvent and separately a water-solvent solution which may be admixed with the recycled solution flowing through line 5 and regenerated in contact zone G1, thus avoiding again the recourse to regeneration by distillation.

Figure 5:
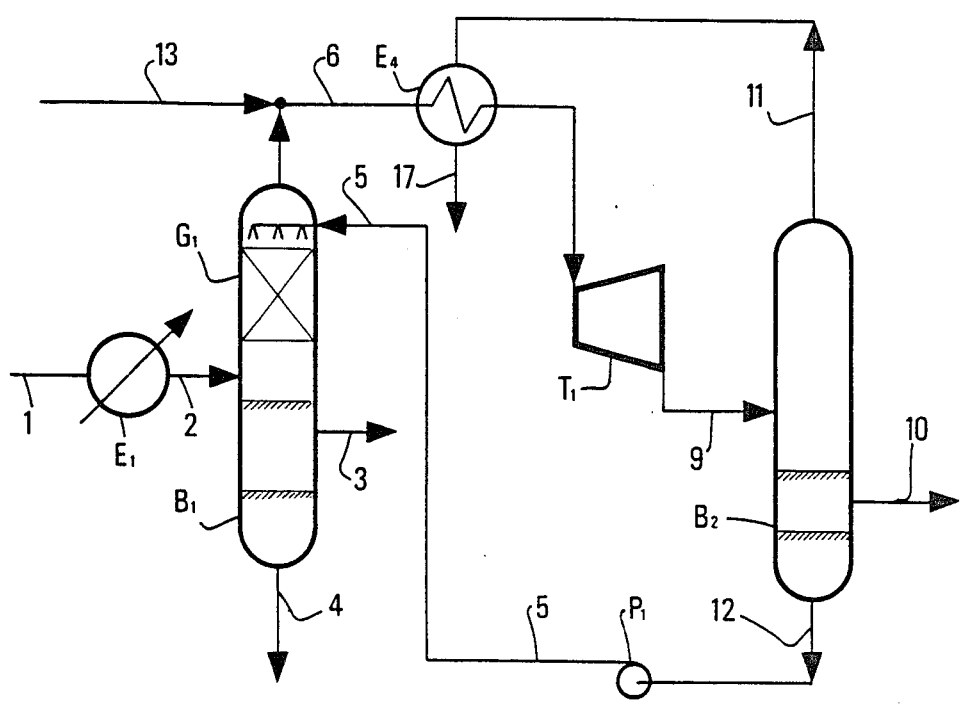
FIG. 5 is a flowsheet illustrating an embodiment wherein the treated gas is cooled through an exchanger and then further cooled by expansion through a turbine before being used as coolant in said exchanger.

In the flowsheet of FIG. 1, the necessary cold is supposed to be supplied to exchanger E2 by a coolant fed through line 7 and discharged through line 8. Other cold sources may also be used according to the process of the invention, particularly those produced by the treated gas itself, such for example as an expansion turbine or an expansion valve. An example of a configuration with an expansion turbine is illustrated in FIG. 5. As compared with the embodiment of FIG. 1, gas cooling is performed by expansion of the gas through a turbine. The gas flowing out from contact zone G1 is cooled in an exchanger E4 by exchange with the treated gas, expanded through turbine T1 with corresponding production of mechanical power, and enters column B2 through line 9. The treated gas is discharged from column B2 through line 11 and heated in exchanger E4, wherefrom it flows out through line 17. The configuration with expansion valve is similar to the configuration with expansion turbine, the turbine being replaced by an expansion valve producing an isenthalpic expansion of the gas.

Different solvents other than methanol may be used.

The solvent must be highly misicible with water and may consist for example of an alcohol other than methanol, such as ethanol, propanol, butanol, a ketone such as acetone or methylethyletone, or still other polar solvents such as N-methylpyrrolidone, dimethylformamide or morpholine.

The solvent may also consist of a mixture of solvents.

It is first essential that the solvent be at least partially miscible (preferably completely miscible) with water and preferably not much miscible with hydrocarbons so as to form two liquid phases during step (b) when the concentration of hydrocarbons other than methane is relatively high. However, with a gas containing a relatively low amount of hydrocarbons other than methane, the process may be applied without producing a liquid hydrocarbon phase. Then it is not complusory that the solvent be miscible with hydrocarbons.

The use of the solvent less volatile than methanol has the advantage of limiting the amount of solvent stripped with the treated gas, for a given cooling temperature. This is advantageous even if the solvent is recovered at the reception terminal since it makes possible to reduce the frequency of the solvent supply on the production site. The less the final cooling temperature is low, the more advantageous is the use of a heavy solvent.

However, when the solvent is less volatile than water, the vapor phase flowing out from contact zone G1 during the regeneration step is usually less rich than the liquid phase recycled through pump P1. It results in incomplete regeneration and the discharged water still contains solvent.

It has been discovered, and this is another object of the invention, that, in particular in the above-mentioned case, it is advantageous to use a solvent forming an azeotrope with water such as ethanol, 2-methoxyethanol, propanol, butanol, propargyl alcohol, pyridine and piperidine.

As a matter of fact, in these conditions, when a liquid phase with a water-solvent composition close to the azeotropic composition is recycled to the regeneration zone, it is possible, during the regeneration step, to strip in vapor phase, at the output of the contact zone G1, a water-solvent mixture substantially of the same composition as that of the recycled liquid phase.

When the solvent is so selected as to form with water an azeotrope comprising relatively little solvent, so as to reduce the solvent losses, the solvent amount stripped in gas phase during the regeneration step becomes relatively low and the solvent concentration of the solution obtained at the end of the cooling step may be insufficient to prevent the formation of hydrates at the lowest cooling temperature.

Figure 2:
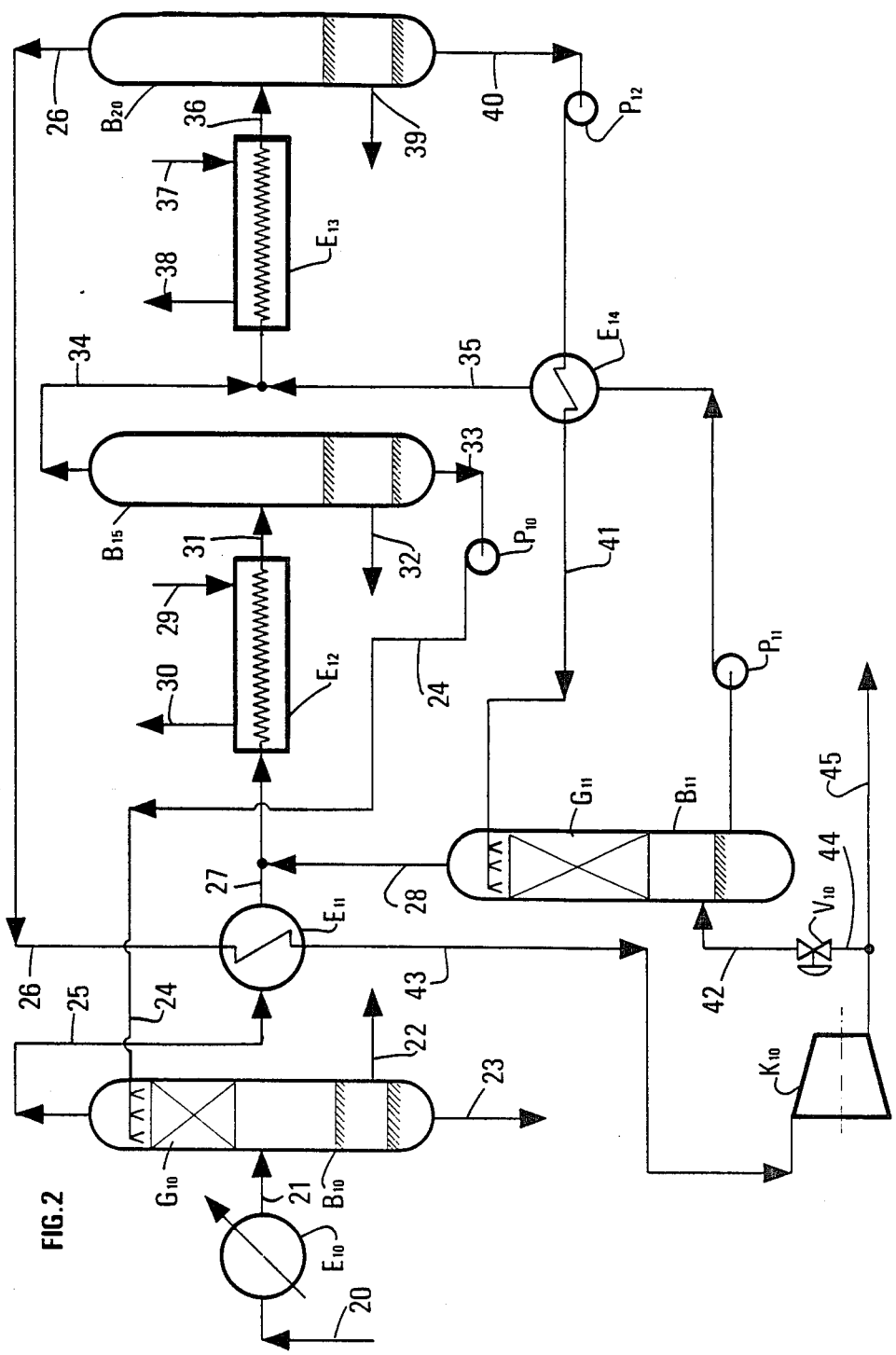
FIG. 2 is a flowsheet illustrating an alternative embodiment of the invention applied to a gas containing methane and condensable hydrocarbons.

It may then be advisable to use the alternative embodiment of the process illustrated in the flowsheet of FIG. 2, here applied to a gas containing methane and condensable hydrocarbons.

The gas to be treated is supplied through line 20. It is cooled with an available coolant (water or air) in exchanger E10 wherefrom it is discharged through line 21, opening into column B10. This first cooling step provides for the separation of a liquid gasoline fraction, formed of hydrocarbons condensable in the temperature and pressure conditions prevailing at the output of exchanger E10, which is discharged through line 22, from an aqueous fraction which settles at the bottom of column B10 and is discharged through line 23. The remaining gas is saturated with water.

The gas is then contacted with a liquid phase formed of the water-containing solvent originating from column B15 and supplied through line 24 to a contact zone G10 formed for example of a packing. The gas discharged from the contact zone is saturated with water and with solvent.

The gas forming out from contact zone G10, saturated with water and solvent, is discharged through line 25.

It is then cooled in exchanger E11 by heat exchange with the treated gas originating from column B20 and supplied through line 26. It flows out from exchanger E11 through line 27 and is admixed with a gas fraction from column B11, conveyed through line 28. The obtained gas mixture is fed to exchanger E12 wherein it is cooled by a coolant supplied through line 29 and discharged through line 30.

It is discharged from exchanger E12 through line 31.

The cooling performed in exchanger E12 provides for the condensation of a LPG fraction which is discharged through line 32. It also provides for the condensation of the major part of water and solvent. There is thus obtained a liquid phase formed of a water and solvent mixture which settles in column B15, is discharged therefrom through line 33 and recycled, through pump P10 and line 24, to the contact zone G10.

In contact zone G10, the liquid phase formed of a solvent-water mixture is counter-currently contacted with a gas saturated with water but containing no solvent. The gas flow rate being much higher than the liquid phase flow rate, the solvent is vaporized and stripped with the gas phase, whereas water is recovered at the bottom of column B10. The separation between water and solvent is thus achieved by contact wtih the gas to be treated.

The gas from column B15 is discharged through line 34 and is subjected to an additional treatment.

It is first admixed with a solvent fraction in liquid phase originating from column B11 and supplied through line 35.

The obtained gas-liquid mixture is subjected to additional cooling in exchanger E13, wherein it is cooled by a coolant fed through line 37 and discharged through line 38.

It flows out from exchanger E13 through line 36 opening in the setting column B20.

The cooling, performed in exchanger E13, produces the condensation of an additional LPG fraction which is discharged through line 39. It also provides for the condensation of an additional water and solvent fraction. The obtained water and solvent mixture has a higher solvent concentration than that recovered through line 33 at the end of the cooling step performed in exchanger E12, as a result of the introduction of liquid solvent through line 35. Accordingly, it is possible to obtain, at the output of exchanger E13, a lower temperature than that obtained at the output of exchanger E12, without risk of hydrate formation. The water and solvent mixture obtained at the output of exchanger E13 settles in column B20, is discharged through line 40 and conveyed through pump 12 to exchanger E14 wherefrom it flows out through line 14 and is supplied to contact zone G11. The countercurrent contact zone G11 is formed, for example, of a packing.

In contact zone G11, the solvent and water mixture supplied through line 41 is contacted with a gas fraction supplied through line 42.

This gas fraction is a part of the treated gas conveyed through line 26 from column B20, which, at the output of exchanger E11, is discharged through line 43 and compressed before being supplied to the compression stage K10.

At the output of the compression stage K10, a fraction of the treated gas is withdrawn through line 44, expanded through expanding valve V10 and supplied to contact zone G11. The major part of the treated gas is discharged through line 45.

The gas fraction of line 45 has a small water and solvent content. The solvent used in this embodiment of the process being heavier than water, the countercurrent contact between the water and solvent mixture supplied through line 41 and the gas fraction supplied through line 42 provides for the stripping of the water admixed with the solvent, said water being found in the gas fraction discharged through line 28, the unvaporized solvent being recovered at the bottom of column B11.

This solvent is discharged through pump P11, passes through exchanger E14, is conveyed through line 35 and admixed with the gas supplied from line 34. It is thus possible, as above mentioned, to obtain to the output of the exchanger E13 a water and solvent liquid phase mixture of higher solvent concentration than the water and solvent mixture recovered at the output of exchanger E12.

The water amount contained in the gas discharged from column B15 through line 34 is small, the required solvent amount to supply through line 35 is also small as well as the gas amount necessary for stripping the liquid phase mixture of water and solvent recovered at the output of exchanger E13.

Finally, this embodiment of the process is characterized in that it comprises the steps (a) to (c) of the basic embodiment. However, before the cooling of step (b), a gas fraction originating from subsequent step (g) is added. Furthermore, this embodiment of the process comprises the (d) to (g) additional following steps of:

(d) Admixing the gas fraction originating from the separation step(c) with a liquid phase solvent-containing fraction originating from step (g).

(e) Cooling the liquid-gas mixture originating from step (d)-thereby producing a liquid fraction essentially formed of solvent and water and a gas fraction.

(f) After the cooling step (e), separating the obtained fractions.

(g) Discharging a part of the gas fraction separated in step (f), as purified gas, and contacting another part of said gas fraction separated in step (f) with at least one part of the solvent-and-water liquid fraction separated in step (f), at a higher temperature than that of step (f), thereby producing a liquid fraction essentially formed of solvent and a gas fraction, and recycling said liquid fraction to step (d) and said gas fraction to step (b).

This embodiment of the process according to the invention is illustrated in example 2.

EXAMPLE 2

In this example, the process is carried out according to the flowsheet of FIG. 2. However, since the treated gas contains only a small amount of hydrocarbons other than methane (dry gas), no condensation of liquid hydrocarbons takes place in columns B10, B15 and B20. The gas to be treated is supplied through line 20 at a temperature of 90° C., a pressure of 5 MPa, and a flow rate of 126,000 kg/h. The gas is saturated with water, its hydrocarbon dew point at a pressure of 5 MPa is lower than −10° C. (dry gas). The gas is cooled by heat exchange with the cooling water in heat exchanger E10 wherefrom it flows out through line 21 at a temperature of 50° C. This cooling produces the condensation of a liquid water fraction. The gas and the aqueous phase are separated in column B10.

The remaining gas, saturated with water, is countercurrently contacted in packing G10 with a liquid phase formed of water-containing solvent originating from column B15 and supplied through line 24. Here the solvent is 2-methoxyethanol of raw formula $C_3H_8O_2$. The water-2-methoxyethanol mixture flows through line 24 at a rate of 340 kg/h. It contains 22.2% by weight of 2-methoxyethanol. The aqueous phase, recovered at the bottom of column B10, flows out through line 23 at a rate of 1560 kg/h. It is formed of a part of the condensed water supplied with gas through line 21 and of water obtained from the gas-liquid contact in packing G10. The gas flowing out from column B10 through line 25, saturated with water and 2-methoxyethanol, is cooled in a first heat exchanger E11 by heat exchange with the treated gas originating from column B20 and supplied through line 26. It flows out from the exchanger through line 27 and is admixed with a gas fraction originating from column B11 and supplied through line 28.

The obtained gas mixture is cooled to a temperature of 15° C. in exchanger E12, by heat exchange with an external coolant supplied through line 29 and flowing out through line 30. It is discharged therefrom through line 31. The successive coolings is exchangers E11 and E12 lead to a condensation of the water-2-methoxyethanol mixture. This liquid phase is separated from the gas in column B15, is discharged through line 33 and conveyed through pump P10 and line 24 towards the packing of column B10. The gas, partially dehydrated, flows out from column B15 through line 34 and is contacted with a water-2-methoxyethanol mixture in liquid phase originating from column B11 and supplied through line 35. This mixture flowing at a rate of 52 kg/h is composed of 60% by weight of 2-methoxyethanol and 40% by weight of water. The obtained gas-liquid mixture is cooled to a temperature of 0° C. in heat exchanger E13 by heat exchange with an external coolant supplied through line 37 and discharged through line 38. It is supplied, through line 36, to column B20. The cooling of the gas-liquid mixture in exchanger E13 provides for the condensation of an additional fraction of water and 2-methoxyethanol. The liquid fraction is separated in column B20 and is discharged therefrom through line 40. This liquid contains 46% by weight of 2-methoxyethanol.

This liquid fraction is supplied through pump P12 to exchanger E14 wherein it is heated by heat exchange with the solution flowing through line 35 and is conveyed through line 41 to the contact zone G11, formed of a packing, where it is contacted with the gas fraction supplied from line 42 at a rate of 4500 kg/h.

The treated gas, freed of the almost entire amount of water and 2-methoxyethanol is discharged from column B20 through line 26, passes through exchanger E11 where it is heated by heat exchange with the gas flowing through lines 25 and 27, flows out through line 43, is recompressed up to 8 MPa in compressor K10 and discharged through line 45 for being delivered. A fraction of said recompressed gas is withdrawn through line 44, expanded at a pressure close to that of the treated gas and supplied to column B11. During the countercurrent contact, in packing G11, with the liquid originating from line 41, the treated gas supplied through line 42, of small water and 2-methoxyethanol content, preferentially increase its water content and is discharged through line 28 to be admixed with the main flow of treated gas originating from line 27. The liquid phase recovered at the bottom of column B11, of higher 2-methoxyethanol concentration than the liquid circulating through line 41, is conveyed through pump P11 to exchanger E14, flows out through line 35 and is admixed with the gas flow of line 34.

The treated gas may eventually contain a relatively high amount of acid gases such as $CO_2$ and $H_2S$ and it may be necessary to reduce this acid gas content.

It is then advantageous to include in the process an additional step of removing acid gases, using the same solvent as that used throughout the process.

Figure 3:
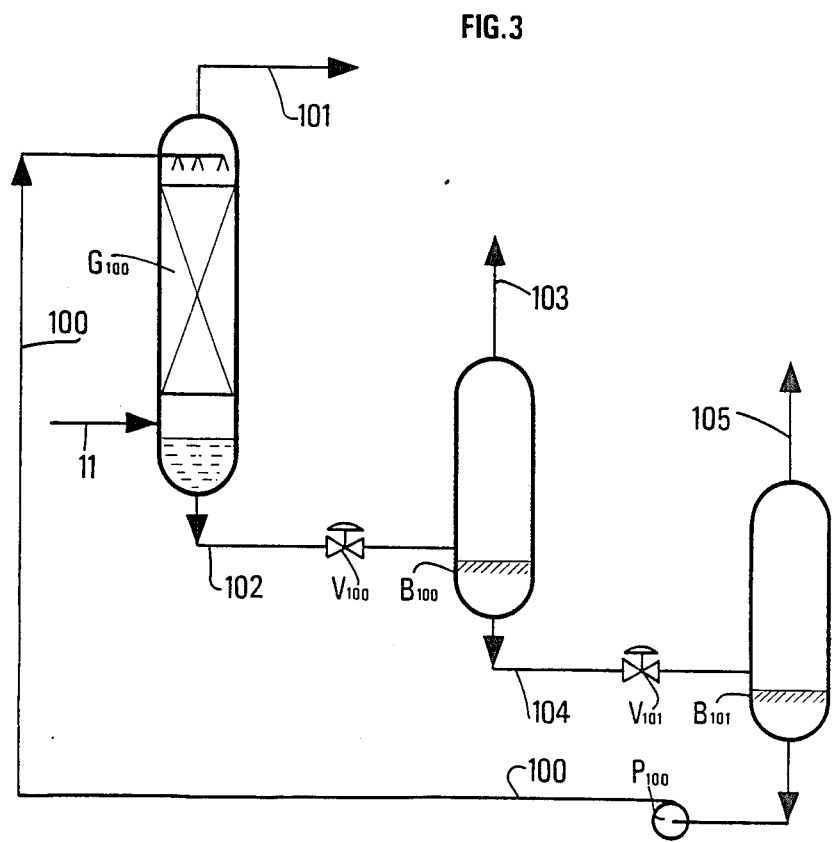
FIG. 3 illustrates an embodiment of the process of the invention comprising an additional step of acid gas removal.

Such a removal of the acid gases may be performed for example in accordance with the flowsheet of FIG. 3.

In the embodiment diagrammatically shown in figure, 1, this step may for example take place at the end of step (c). The gas discharged through line 11 is counter-currently contacted with the solvent phase fed through line 110 to contact zone G100 formed for example of a packing.

The gas discharged through line 101 is substantially free of acid gases. The solvent phase containing acid gases is regenerated by mere expansion. For reducing the solvent losses, it is advantageous to proceed with successive expansions. In the diagram of FIG. 3, the regeneration is performed in two successive expansions. At the end of the first gas expansion (line 102) through the expansion valve V100, the obtained gas phase and liquid phase are separated in column B100. The gas phase is discharged through line 103.

The liquid phase is discharged through line 104 and again expanded through valve V101. The obtained gas phase and liquid phase are separated in column B101. The gas phase is discharged through line 105. The liquid phase is discharged through line 100 and recycled to the contact zone G100 through pump P100.

The solvent rate is necessarily higher than that used during step (a) of the process. Thus when the solvent is methanol, the molar ratio of the solvent flow rate to the flow rate of treated gas is typically of about 0.5. This ratio is usually from 0.1 to 1.

However, it is preferred here to avoid recourse to distillation, since the solvent regeneration during this step may be performed by expansion.

During successive expansions, the pressure stage levels are provided ar regular intervals in the range from the higher pressure close to the pressure of the treated gas to the lower expansion pressure which may be close to atmospheric pressure.

The additional step introduced in this embodiment of the process is hence characterized in that the gas obtained in the preceding steps is contacted with a sufficient flow of solvent to strip the acid gases to be removed, the solvent phase resulting from this washing operation being regenerated by one or more successive expansions and recycled.

The washing operation is advantageously performed at a temperature close to the temperature of the gas feeding the contact zone. Thus when performed at the end of step (c) of the process, it is advantageously conducted at a temperature close to the temperature obtained at the end of step (b). This is advantageous, particularly when the solvent is methanol, since the solvent may then be used under conditions of better selectively and of reduced solvent loss.

During the successive expansions for solvent regeneration, the acid gases removed through lines 103 and 105, may strip solvent vapors, thus resulting in a solvent loss. These solvent traces in gas phase may be recovered by washing the acid gases with water so as to absorb the solvent traces. The solvent aqueous solution obtained after said washing may be, as for the LPG liquid phase washing, reinjected in the recycled solution flowing through line 5 and may be regenerated in contact zone G1, thus avoiding again a regeneration by distillation.

By the provision of said additional step at the end of step (a) it is also possible to proceed at a higher temperature which may be more convenient with a solvent whose boiling temperature is relatively high.

In the second embodiment of the process described with reference to the diagram of FIG. 2, the additional step of acid gas removal is preferentially performed at the end of step (e) on the gas originating from the gas-liquid separation performed during step (f), before heating of the gas by internal exchange, but it may also take place at the end of step (c) or of step (a).

Different arrangements are thus possible which will be selected in accordance with the composition of the gas to be treated and with the nature of the required specifications for the gas obtained after treatment.

The process according to the invention is applicable to natural gas. When said natural gas is a gas with condensate, the purpose is to adjust the water dew point, the hydrocarbon dew point and optionally to simultaneously produce a hydrocarbon liquid fraction.

The treated gas may also be an associated gas whose treatment conditions are similar to those of a gas with condensate.

The treated gas may also be a so-called "dry" gas, i.e. not producing a hydrocarbon liquid fraction under normal production conditions, the first main purpose being then to adjust the water dew point.

The invention is also applicable to a refinery gas such as a "fuel gas" originating from conversion units which may also contain hydrogen.

The purpose will be then to provide for the dehydration and/or the separation of a hydrocarbon liquid fraction.

In step (a) of the process according to the invention, the pressure of the treated gas may vary within a wide range from 1 to 200 bars, the temperature being selected for example between 0° and 100° C., preferably between 10° and 50° C.

What is claimed as the invention is:

1. A process for the treatment of a methane and water-containing gas in order to remove at least a part of said water from the gas, comprising the steps of:
   (a) contacting said gas with a recycled liquid phase containing both water and introduced solvent, said solvent being a non-hydrocarbon compound other than water and being miscible with water, maintaining contact conditions adapted to vaporize and transfer to the gas at least 90% of the introduced solvent amount originating from the recycled liquid phase, discharging the liquid aqueous phase resulting from said contact and containing less than 10% of the introduced solvent amount, and recovering a gas containing in a vaporized state at least 90% of the introduced solvent amount;
   (b) cooling the gas obtained in step (a), to condense a liquid fraction essentially formed of solvent and water;
   (c) separating residual uncondensed gas from said liquid fraction and recycling to step (a) resultant separated liquid fraction containing solvent and water, to form the recycled liquid phase.

2. A process according to claim 1, wherein the molar ratio of the solvent flow rate to the flow rate of treated gas during step (a) ranges from 1/1000 to 1/10.

3. A process according to claim 1, wherein the solvent is an alcohol.

4. A process according to claim 1, wherein the solvent is methanol.

5. A process according to claim 1, wherein the solvent is a solvent forming an azeotrope with water.

6. A process according to claim 1, wherein the solvent is ethanol, 2-methoxyethanol, propanol, butanol, propargyl alcohol, pyridine, or piperidine.

7. A process according to claim 1 wherein step (a) is conducted in a vertical column and the contact is counter-current between rising gas and descending recycled liquid phase.

8. A process according to claim 1, wherein before cooling in step (b), a gas fraction originating from subsequent step (g) is added to the gas obtained in step (a), and:

(d) the residual gas originating from the separation step (c) is admixed with a fraction containing solvent in liquid phase originating from step (g);

(e) the liquid-gas mixture originating from step (d) is cooled so as to produce a liquid fraction essentially formed of solvent and water and a gas fraction;

(f) the obtained fractions are separated after the cooling step (e), and (g) a part of the gas fraction separated in step (f) is discharged as purified gas and another part of said gas fraction separated in step (f) is contacted with at least a portion of the solvent and water liquid fraction separated in step (f), at a temperature higher than that of step (f), thus producing a liquid fraction essentially formed of solvent and a gas fraction, and recycling said liquid fraction to step (d) and adding said gas fraction to the gas obtained in step (a).

9. A process according to claim 1, applied to a gas further containing at least one hydrocarbon other than methane, condensable in the conditions of step (b) by forming a hydrocarbon liquid fraction separate from said fraction consisting essentially of solvent and water, and said hydrocarbon liquid fraction is separated and discharged from the process.

10. A process according to claim 9, wherein the hydrocarbon liquid fraction formed during step (b) is contacted with water so as to transfer to water at least a part of the solvent dissolved in the hydrocarbon liquid fraction, so as to obtain a hydrocarbon liquid phase at least partially free of solvent and a water and solvent liquid phase which may be admixed to the liquid phase recycled from step (c) to step (a).

11. A process according to claim 1, wherein the treated gas is subjected to an additional treatment step for removing at least a portion of acid gases present in said gas, the treated gas being contacted with solvent in sufficient amount to dissolve the acid gases to be removed and the solvent phase obtained from this contact operation being expanded so as to produce at least one gas fraction which is removed and a liquid phase which is recycled to said additional treatment.

12. A process according to claim 10, wherein gas fraction obtained after expansion of the solvent is contacted with water so as to transfer to water at least a portion of the solvent contained in said gas fraction, the obtained water and solvent solution being admixed with the liquid phase recycled from step (c) to step (a).

13. A process according to claim 1, wherein the solvent is added to the gas obtained in step (a), before proceeding to step (b), in sufficient amount to compensate for the losses and to maintain a stable operation.

14. A process according to claim 1, wherein the contact conditions are so selected as to maintain a solvent concentration from 0.01 to 5% by weight in the aqueous liquid phase discharged from step (a).

15. A process according to claim 1, wherein the gas to be treated is divided into two parts before step (a), only a fraction of the total amount of the gas to be treated is contacted with the recycled liquid phase, the other gas fraction being admixed with the gas recovered after contact with the recycled liquid phase.

16. A process according to claim 13, wherein the portion of treated gas contacted with the recycled liquid phase amounts to 15-50% of the total amount of gas to be treated.

17. A process according to claim 1, wherein the required cooling of step (b) is obtained at least partly by expanding at least a portion of the treated gas through an expansion turbine and/or an expansion valve.

* * * * *